United States Patent [19]

Parab

[11] Patent Number: 5,702,711
[45] Date of Patent: Dec. 30, 1997

[54] METHOD FOR ENHANCING THE RATE OF SKIN PERMEATION OF LACTIC ACID THROUGH USE OF THE L-ENANTIOMER

[75] Inventor: Prakash Parab, Williamsville, N.Y.

[73] Assignee: Bristol-Myers Squibb Company, New York, N.Y.

[21] Appl. No.: 452,483

[22] Filed: May 26, 1995

Related U.S. Application Data

[63] Continuation of Ser. No. 215,985, Mar. 22, 1994, abandoned.

[51] Int. Cl.$^6$ .............. A61K 7/00; A61K 31/19
[52] U.S. Cl. .............. 424/401; 514/557; 514/844; 514/846
[58] Field of Search .............. 424/401; 514/557, 514/553, 844, 846

[56] References Cited

U.S. PATENT DOCUMENTS

| | | | |
|---|---|---|---|
| 4,021,572 | 5/1977 | Van Scott | 424/317 |
| 4,285,964 | 8/1981 | Niebes | 424/283 |
| 4,363,815 | 12/1982 | Yu | 424/274 |
| 5,091,171 | 2/1992 | Yu | 424/642 |
| 5,100,918 | 3/1992 | Sunshine | 514/557 |
| 5,254,343 | 10/1993 | Parab | 424/401 |

FOREIGN PATENT DOCUMENTS 1120860  3/1982  Canada.

*Primary Examiner*—Gollamudi S. Kishore
*Attorney, Agent, or Firm*—Morton S. Simon

[57] ABSTRACT

Methods of increasing the rate of lactic acid permeation in skin for the treatment of dermatological disorders by applying a composition containing an inorganic or organic salt of lactic acid in a dermatologically acceptable composition wherein at least 70% of the lactic acid moiety in the salt is L-lactic acid, and compositions for practicing such methods.

13 Claims, 2 Drawing Sheets

METHOD FOR ENHANCING THE RATE OF SKIN PERMEATION OF LACTIC ACID THROUGH USE OF THE L-ENANTIOMER

This application is a continuation of application Ser. No. 08/215,985, filed Mar. 22, 1994 now abandoned.

FIELD OF THE INVENTION

This invention relates to topical administration of therapeutic compositions for the treatment of determatological disorders, to compositions employed for such administration and to methods of preparing such compositions. More particularly, it relates to topical administration of therapeutically effective amounts of L-lactic acid salts under conditions such that there is rapid and higher skin permeation of the L-lactic acid.

BRIEF DESCRIPTION OF THE PRIOR ART

The topical use of α-hydroxy acids and α-keto acids for the treatment of various skin conditions is well known in the art. It is described, for example in U.S. Pat. Nos. 3,879,537, 4,105,783 and 4,363,815.

U.S. Pat. No. 5,091,171 describes the employment of salts of various α-hydroxyacids and α-keto acids with amines, especially amphoteric amines, including amino acids, dipeptides, polypeptides and proteins. Typical therapeutically useful salts described in the patent include, for example, lysine lactate, a salt obtained by reaction between lysine and the α-hydroxyacid, lactic acid. Other salts include aliphatic, aromatic and heterocyclic amino acids; dibasic and diacidic amino acids; substituted and unsubstituted amino acids as well as synthetic and natural amino acids. The prior art recognizes that α-hydroxy acids exist in enantiomeric forms and racemic mixtures, but there is no recognition of a distinction between the skin permeation and, hence, the therapeutic efficacy of the enantiomers and racemic mixtures. More specifically, there is no recognition in the prior art of the discovery described and claimed herein, namely that the L-form of lactic acid is more efficient for permeating mammalian skin than is the D-form.

SUMMARY OF THE INVENTION

Figure 1:
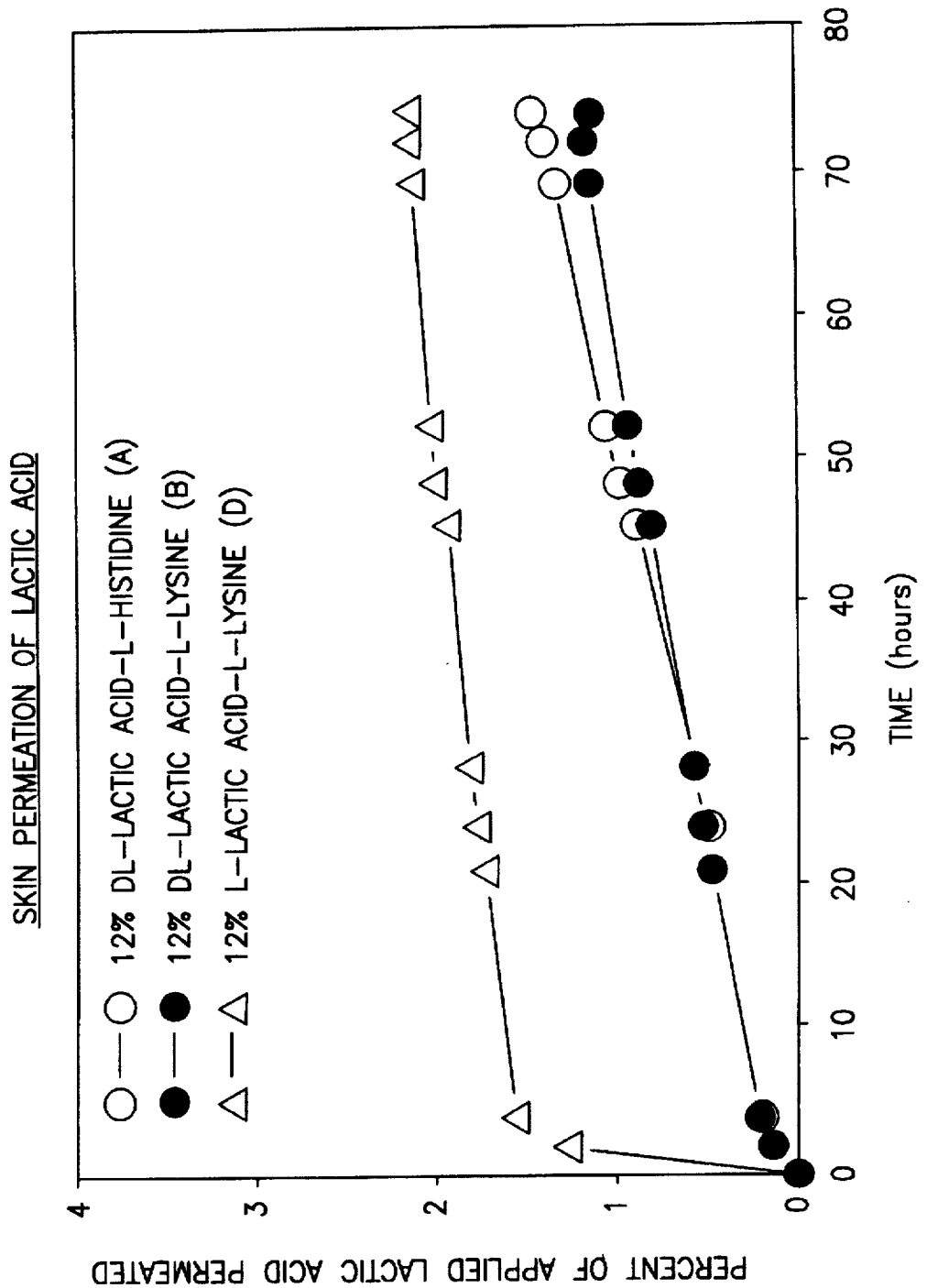
FIGS. 1 and 2 are graphs which will assist in understanding the improved properties of the compositions and methods of this invention.

Novel compositions and methods for the treatment of dermatological disorders have now been discovered. The compositions comprise a dermatologically effective amount of a salt of L-lactic acid together with a dermatologically acceptable topical carrier. The most preferred compositions are substantially free of salts of D-lactic acid. More specifically, the salt of lactic acid in such compositions is substantially only in the L-form. However, as will be explained more fully hereinafter, compositions containing a salt of L-lactic acid and a salt of D-lactic acid are useful provided at least about 70% of the lactic acid component in such compositions is in the L-form.

Generally, the pH of the novel compositions is such as to permit salt formation with the inorganic or organic base employed. Optimum pH, therefore will depend upon the basicity of the selected salt forming base. Usually, the pH of the composition will be from about 2.5 to 9, preferably 3.5 to 7 and most preferably from 4 to 5.5. These pH ranges permit salt formation with preferred bases.

It has been further discovered that topical administration of a composition of the present invention to patients in need of such administration promotes more rapid permeation of the lactic acid into the skin and a higher concentration of lactic acid in the skin during observed time periods.

The compositions employed in this invention are useful for all known utilities for topical administration of α-hydroxyacids. These include, for example, treatment of dry skin, xerosis, ichthyosis, dandruff, acne, keratoses, psoriasis, wrinkles, warts, blemished skin, eczema, age spots, laxity, leathery texture, roughness, sallow complexion, scaling, telangiectasia, mottled pigment, skin atrophy caused by steroids, hyperpigmented skin, inflammatory dermatoses, skin changes associated with intrinsic ageing and photodamage, and skin cleansing.

In addition to the L-lactic acid salt, the compositions of the invention may contain any of a large number of auxiliary cosmetic and pharmaceutical agents, provided that such additional agents are inert with respect to the formation, stability and activity of the L-lactic acid salts of the invention, i.e., they are reaction inert.

Cosmetic and pharmaceutical agents include those that improve or eradicate age spots, keratoses and wrinkles; analgesics; anesthetics; antiacne agents; antibacterials; antiyeast agents; antifungal agents; antiviral agents; antidandruff agents; antidermatitis agents; antipruritic agents; antiinflammatory agents; antihyperkeratolytic agents; antidryskin agents; antiperspirants; antipsoriatic agents; antiseborrheic agents; hair conditioners and hair treatment agents; antiaging and antiwrinkle agents; antiphotoaging agents; antiasthmatic agents and bronchodilators; sunscreen agents; antihistamine agents; skin lightening agents; depigmenting agents; vitamins; corticosteroids; tanning agents; hormones; retinoids; topical cardiovascular agents and other dermatologicals.

Examples of typical cosmetic and pharmaceutical agents are clotrimazole, ketoconazole, miconazole, griseofulvin, hydroxyzine, diphenhydramine, pramozine, lidocaine, procaine, mepivacaine, monobenzone, erythromycin, tetracycline, clindamycin, meclocycline, hydroquinone, 4-hydroxyanisole, minocycline, naproxen, ibuprofen, theophylline, cromolyn, albuteral, all trans retinoic acid, 13-cis retinoic acid, hydrocortisone, hydrocortisone 21-acetate, hydrocortisone 17-valerate, hydrocotisone 17-butyrate, betamethasone valerate, betamethasone dipropionate, triamcinolone acetonide, fluocinonide, clobetasol propionate, halobetasol propionate, benzoyl peroxide, crotamiton, propranolol, promethazine, vitamin A palmitate, vitamin E acetate and calcipotriene.

The term "dermatological disorders", as used herein, refers to any of those mentioned above as well as other conditions treated by cosmetologists or dermatologists with α-hydroxy acids or salts thereof. It includes skin conditions the treatment of which might usually be regarded as cosmetic, such as treatment of hyperpigmented skin areas, as well as more serious skin conditions such as chronic and acute psoriasis.

The salts of this invention may be employed with any of a variety of dermatologically acceptable carriers or excipients normally employed with compositions for topical administration. These are well known to the skilled artisan and include, for example, surfactants, emulsifiers, stabilizers, preservatives, antiseptics, emollients, thickeners, lubricants, humectants, chelating agents, fragrances and skin permeation enhancers.

The compositions may be in the form of solutions, emulsions, suspensions, lotions, creams, gels, ointments, liposomes, aerosol sprays, polymeric gels, sticks, plasters, patches, films or tapes, the preparation of which are well known to those skilled in the art of topical formulations.

Examples of suitable emulsifiers include, steareth-2, steareth-21, polyoxyethylene-4-lauryl ether, polyethylene glycol-23-lauryl ether, sorbitan monostearate and polyoxyethylene-20-sorbitan monostearate. Examples of preservatives include, methyl paraben, propyl paraben, sorbic acid, potassium sorbate, benzyl alcohol, diazolidinyl urea, methylisothiazolinone and methylchloroisothiazolinone.

Examples of emollients include, silicone oils, mineral oil, cocoa butter, hexyl laurate, diisopropyl adipate, dibutyl adipate, glyceryl stearate, beeswax, lanolin, sperm wax, cetyl palmitate, isopropyl myristate, isopropyl palmitate, isopropyl isostearate and propylene glycol dioctanoate.

Among the thickening agents there may be mentioned, byway of example, xanthan gum brine tolerant (xanthan gum BT), xanthan gum and gum acacia, all of which are excellent as emulsion stabilizers and gelling agents.

Acceptable humectants include, for example, propylene glycol, glycerin, butylene glycol and polyethylene glycols.

As will be recognized by the skilled artisan, the term "effective amount" relates to the condition under treatment. Some conditions may require treatment with large amounts of L-lactic acid salts. Others may be effectively treated with smaller amounts. The treatment may require one or multiple dosage units applied all at once or over a period of time. Generally, the dosage requirements will be of the order of magnitude normally employed with similar treatments using α-hydroxyacids. However, because of the rapid onset of permeation and higher permeation concentration achieved, it is often possible to use lesser amounts of α-hydroxy acid salts in accordance with the procedures of this invention. In any event, the skilled artisan will have no difficulty in determining an "effective amount" for the treatment of a specific condition, by the application of the routine test procedures normally employed.

DETAILED DESCRIPTION OF THE INVENTION

The advantages of this invention will be readily apparent from the following description taken together with the results illustrated in the figures.

The compositions tested are shown in the following Table 1. The formulations in this table and subsequent tables are represented by capital letters. Those represented by the same letter in different tables are identical formulations.

The compositions were prepared by mixing the identified forms of the lactic acid and the selected amino acid together with water until uniform. The mixture was heated to a temperature of 60°–65° C. with mixing for 25 minutes. Mixing was continued while cooling to room temperature and the necessary amount of water was added. The pH was then measured.

TABLE 1

Composition of solution formulations containing L-lysine and L-histidine salts of 12% DL and L-lactic acid.

| Ingredients | A | B | C | D |
|---|---|---|---|---|
| DL-Lactic Acid (88%) | 13.6 | 13.6 | — | — |
| L-Lactic Acid (88%) | — | — | 13.6 | 13.6 |

TABLE 1-continued

Composition of solution formulations containing L-lysine and L-histidine salts of 12% DL and L-lactic acid.

| Ingredients | A | B | C | D |
|---|---|---|---|---|
| L-Histidine | 16.52 | — | 16.52 | — |
| L-Lysine Monohydrate | — | 16.14 | — | 16.14 |
| Water QS | 100.00 | 100.00 | 100.00 | 100.00 |
| pH | 4.75 | 4.63 | 4.81 | 4.69 |

The capacity of the various compositions to penetrate the epidermis was tested by the following standard procedure.

In-vitro Skin Permeation Study $^{14}$C-L-lactic acid sodium salt and $^{14}$C-DL-lactic acid sodium salt were used in the skin permeation study. The formulations with L-lactic acid salts and DL-lactic acid salts were spiked with $^{14}$C-L-lactic acid sodium salt and $^{14}$C-DL-lactic acid sodium salt, respectively, to result in a radioactive concentration of 6 micro curie per ml.

Skin Preparation

Excised human cadaver skin samples obtained from the New York Firefighters Skin Bank were used. The skin was supplied as sterile, split-thickness skin with most of the underlying dermis already removed. The skin samples were thawed for 15 minutes at room temperature and then transferred and rinsed in normal saline for 30 minutes. Appropriate size specimens were sectioned into squares to fit the diffusion cells.

Franz Diffusion Cell Study at Finite Dose

For each formulation, the skin section was mounted on three or four flat flange Franz diffusion cells (FDC 400) with a diffusional cross-section area of 1.2 cm$^2$. A 100 micro liter sample of test formulation was placed on the stratum corneum surface of the skin in the donor compartment and the receptor compartment was filled with about 11 ml of normal saline. The receptor fluid was well stirred throughout the experiment and the temperature was maintained by circulating water at 37° C. through the water jacket of the diffusion cells. Precisely 500 µl of receptor fluid was collected in a scintillation vial at appropriate intervals over a period of about 73 hours. Fifteen ml of scintillation fluid (INSTA-GEL XF, PACKARD) were added directly to the scintillation vial and the lactic acid content was determined on a Beckman LS 3801 scintillation counter. The receptor fluid was replenished after each withdrawal. All the receptor fluid and replenished fluids were filtered using a 0.22 µm filter and thoroughly degassed before use.

FIG. 1 shows the results of a skin permeation study comparing compositions containing:

12% solution of the L-histidine salt of DL-lactic acid

12% solution of the L-lysine salt of DL-lactic acid

12% solution of the L-lysine salt of L-lactic acid

It will be seen that over the course of about 70 hours, the permeation of DL-lactic acid (DL-LA), whether as a salt with L-histidine (L-His) or with L-lysine (L-Lys), was essentially the same. In contrast, over the complete course of the study, the degree of permeation of L-lactic acid (L-LA) as a salt with L-lysine was rapid in onset and much higher than with the other compositions.

Table 2 summarizes the results shown in FIG. 1. From the table, it is clear that at 4 hours and 73 hours, the skin permeation of L-lactic acid (as the L-lysine salt) is about 7.5 fold and 2 fold higher than that of the corresponding DL-lactic acid salt. It is also clear that L-lactic acid permeated faster and to a higher level than DL-lactic acid from their respective L-lysine salt solutions and that there is practically no difference in the permeation profile of the DL-lactic acid from either the L-lysine or L-histidine lactate solutions.

TABLE 2

In vitro skin permeation of L-lactic acid and DL-lactic acid from different formulations.

| Formulation | Amount Permeated (mcg/cm²) | | Amount permeated relative to DL-LA-L-Lysine control | |
|---|---|---|---|---|
| | 4 Hours | 73 Hours | 4 Hours | 73 Hours |
| B | 21 | 119 | 1.0 | 1.0 |
| D | 158 | 223 | 7.5 | 1.9 |
| A | 18 | 143 | 0.9 | 1.2 |

Similar results are achieved if the L-lactic acid salts are prepared from either enantiomer of histidine or lysine or from racemic mixtures of these amino acids. The essence of the invention is the L-lactic acid anion not the geometric arrangement of the atoms in the cation.

Figure 2:
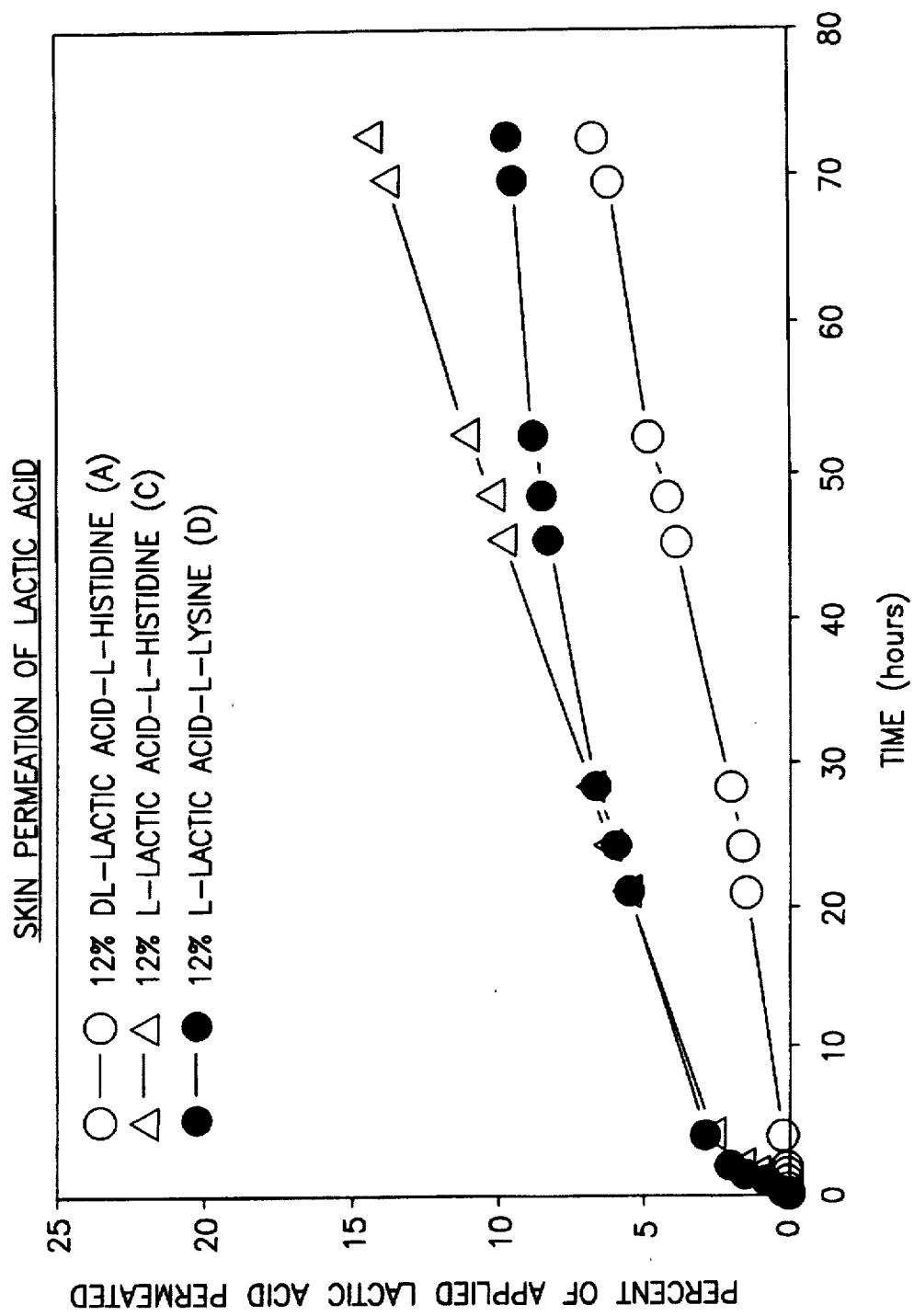

FIG. 2 shows the results of a further study comparing:
12% solution of the L-Histidine salt of DL-lactic acid
12% solution of the L-Histidine salt of L-lactic acid
12% solution of the L-Lysine salt of L-lactic acid.

It is again seen that there is a rapid onset of permeation and a consistently higher degree of permeation for the L-lactic acid as a salt of L-histidine compared to DL-lactic acid as a salt of L-histidine.

Table 3 summarizes the results shown in FIG. 2. From the table, it is clear that at 4 hours and 73 hours, the skin permeation of L-lactic acid (as the L-histidine salt) is about 10.3 fold and 2.1 fold higher than that of the corresponding DL-lactic acid salt. Overall the rank order of skin permeation is L-LA-L-His>L-LA-L-Lys>DL-LA-L-His. In each instance, the L-lactic acid salt has higher degree of permeation and more rapid onset than DL-lactic acid salt.

The permeation of L-lactic acid can be further improved in comparison to DL-lactic acid by selecting appropriate cations. The $NH_4^+$, $Na^+$, $K^+$, cations are preferred over L-lysine and L-histidine, because of their small molecular weight compared to amino acids, because they are more readily available and because they provide consistently good results.

TABLE 3

In vitro skin permeation of L-lactic acid and DL-lactic acid from different formulations

| Formulation | Amount Permeated (mcg/cm²) | | Amount permeated relative to DL-LA-L-His control | |
|---|---|---|---|---|
| | 4 Hours | 73 Hours | 4 Hours | 73 Hour |
| A | 23 | 631 | 1.0 | 1.0 |
| C | 237 | 1309 | 10.3 | 2.1 |
| D | 293 | 994 | 12.7 | 1.6 |

It will be noted by a comparison of the second columns in Tables 2 and 3 that there are appreciable differences in the amounts of permeated products under what appear to be identical conditions. This apparent anomaly arises because different skin samples were employed in the tests. The skilled artisan will know that there are large variations in skin porosity and that tests of the nature employed herein are only valid when, as here, identical skin samples are compared.

The salts of this invention may be obtained by standard procedures by reaction between L-lactic acid and any of variety of inorganic alkali and organic bases.

Any of a wide variety of inorganic alkali bases or organic bases may be employed to form the inorganic and organic salts of this invention, and such salts will be prepared by simple acid/base reactions using procedures well known to the skilled artisan. Alkali and alkaline earth metal salts, such as Na, K, Ca, Mg and Li hydroxides, oxides, carbonates, bicarbonates and others may be utilized. Ammonium salts, particularly ammonium hydroxide, are useful as are quaternary ammonium compounds such as tri-alkylammonium hydroxide. Organic nitrogen bases, including both natural and synthetic amino acids, peptides, polypeptides, and proteins, are useful. Other nitrogen containing bases which may be employed to produce the salts include, organic bases with imino, guanidino, imidazolino, imidazolyl, or other equivalent functionality. Various primary, secondary and tertiary amines, particularly those substituted with $C_{1-8}$ alkyl or aryl groups, may be utilized. Preferred amines include, alkanolamines mono-, di- and tri-substituted amines such as propyl and dipropyl amine, aniline, methyl aniline and propyl aniline, pyridine, dialkanolamines, alkylalkanolamines, rialkylamines and trialkanolamines.

The useful salts of the invention also include amphoteric salts of L-lactic acid, such as, lecithin, phosphotidyl ethanolamine, phosphatidyl serine and sphingomyelin salts. They also include salts prepared from ornithine, arginine, carnosine (alanyl- histidine), 4-aminobutanoic acid and citrulline (α-amino α-ureidovaleric acid).

Representative amino acid salts of lactic acid include, for example, glycine, alanine, valine, leucine, isoleucine, serine, threonine, cysteine, cystine and tryptophan. The most preferred are salts of the basic amino acids lysine, histidine and arginine.

The important criterion in selecting the counter ion of the salts of the invention is that the base from which they are formed have a low $PK_b$ value. The base must be a sufficiently strong to counteract the acidity of lactic acid. Lactic acid is a weak acid. A 1M aqueous solution of lactic acid has a pH of 1.9. As stated above, the pH of the compositions of this invention is such as to ensure salt formation. Generally, it is from about 2.5 to 9. Preferably it is from 3.5 to 7 and most preferably it is from 4 to 5.5.

The concentration of L-lactic acid salt in the enantiomer mixtures of the invention is at least about 70%. Preferably it is 85%. Most preferably, it is about 100%, i.e. the compositions are substantially free of D-lactic acid salts.

The crux of this invention is the unexpected discovery that L-lactic acid, as the sole lactic acid component, or in a mixture containing both L-lactic acid and D-lactic acid, when in the form of selected salts of either enantiomer, permeates mammalian skin at a higher rate than D-lactic acid. Thus, when a topical mixture containing a major portion of an L-lactic acid and a minor portion of a D-lactic acid is applied to human skin, the L-lactic acid salt permeates the skin at a higher rate than the D-lactic acid salt. As a result the proportion of L-lactic acid salt in the skin compared to the D-lactic acid salt will be higher than the proportion of these enantiomers in the form of their salts in the composition.

The most preferred compositions of this invention will contain 100% of the selected lactic acid salt in the L-form.

However, there is a tendency for pure L-lactic acid to spontaneously racemize with time to form an equilibrium mixture containing about 85% of the L-enantiomer and about 15% of the D-enantiomer. Such mixtures are useful to form the compositions of this invention.

At the present time, lactic acid is commercially available in solutions containing 85 to 90% lactic acid in the D-form, or in the L-form or as a racemic mixture. It is most convenient to use these solutions for the preparation of compositions of this invention. The solutions can be mixed in accordance with procedures readily apparent to the skilled artisan to produce lactic acid solutions with a preselected proportion of L-lactic acid and then converted to the selected salt. Thus, for example, an L-lactic acid solution can be mixed with a DL-lactic acid solution to prepare a solution containing 70% L-lactic acid and 30% D-lactic acid.

These mixtures are useful for the formation of the compositions of the invention. They can be used directly or can be converted by well known means to dermatological compositions of the invention such as lotions, creams, ointments and the like, for topical administration to patients in need of treatment for dermatological disorders.

What is claimed is:

1. A method of increasing the rate of L-lactic acid permeation in mammalian skin comprising applying to said skin a composition containing a therapeutic amount of a mixture of an inorganic or organic lactate salt in a dermatologically acceptable carrier, 100% by weight of the lactate salt being an L-lactate salt.

2. A method of increasing the rate of L-lactic acid permeation in mammalian skin, comprising applying to said skin a composition containing a therapeutic amount of a mixture of an inorganic or organic lactate salt in a dermatologically acceptable carrier, from about 70% to about 100% by weight of the lactate salt being an L-lactate salt.

3. The method as claimed in claim 2 wherein the salt of lactic acid is an organic salt.

4. The method as claimed in claim 3 wherein the salt is a salt of an amino acid.

5. The method as claimed in claim 4 wherein the amino acid is selected from the group consisting of lysine and histidine.

6. The method as claimed in claims 1, 2, 3, 4 or 5 wherein the composition has a pH of from 2.5 to 9.

7. The method as claimed in claim 1, 2, 3, 4 or 5 wherein at least about 85% of the lactic acid moiety is L-lactic acid.

8. The method as claimed in claim 1, 2, 3, 4 or 5 wherein the composition has a pH of from about 3.5 to 7 and at least about 85% of the lactic acid moiety of is L-lactic acid.

9. The method as claimed in claim 2 wherein salt of lactic acid is an inorganic salt.

10. The method as claimed in claim 9 wherein the salt is selected from the group consisting of ammonium, sodium and potassium salts.

11. The method as claimed in claim 9 or 10 wherein the composition has a pH of from 2.5 to 9.

12. The method as claimed in claim 9 or 10 wherein at least about 85% of the lactic acid moiety is L-lactic acid.

13. The method as claimed in claim 9 or 10 wherein the composition has a pH of from about 3.5 to 7 and at least about 85% of the lactic acid moiety is L-lactic acid.

* * * * *